United States Patent
Salyer et al.

(10) Patent No.: US 6,730,094 B2
(45) Date of Patent: May 4, 2004

(54) CUTTING EDGES FOR REAMERS AND A METHOD FOR MAKING SAME

(75) Inventors: Paul E. Salyer, Warsaw, IN (US); Todd Wolford, Goshen, IN (US)

(73) Assignee: Symmetry Medical USA, Inc., Warsaw, IN (US)

(*) Notice: Subject to any disclaimer, the term of this patent is extended or adjusted under 35 U.S.C. 154(b) by 110 days.

(21) Appl. No.: 10/047,946

(22) Filed: Jan. 14, 2002

(65) Prior Publication Data
US 2003/0135219 A1 Jul. 17, 2003

(51) Int. Cl.[7] ............................................... A61B 17/00
(52) U.S. Cl. ............................................. 606/80; 606/81
(58) Field of Search ............................ 606/79, 80, 81, 606/87, 86

(56) References Cited

U.S. PATENT DOCUMENTS

| 5,919,195 A | * | 7/1999 | Wilson et al. ............... 606/80 |
| 6,277,121 B1 | * | 8/2001 | Burkinshaw et al. ......... 606/80 |
| 6,475,221 B1 | * | 11/2002 | White et al. ................ 606/80 |

* cited by examiner

Primary Examiner—Cary E. O'Connor
Assistant Examiner—Candice C. Melson
(74) Attorney, Agent, or Firm—Taylor & Aust, P.C.

(57) ABSTRACT

A new and improved reamer having a plurality of openings therein. Each of the openings have a periphery and a cutting edge selected from the periphery. Each of the cutting edges are bound by opposite portions of the periphery. The opposite portions are extended past the cutting edge in a direction opposite of the direction transverse of the cutting edge whereby the cutting edge may be shaped as desired independently of the shape of the periphery.

41 Claims, 3 Drawing Sheets

CUTTING EDGES FOR REAMERS AND A METHOD FOR MAKING SAME

BACKGROUND OF THE INVENTION

1. Field of the Invention

The present invention relates to reamers, and, more particularly, to acetabular reamers, patella reamers and glenoid reamers, cutting edges on such reamers and methods of making the cutting edges.

2. Description of the Related Art

Reamers are used by surgeons to prepare bones for receiving components of artificial joints. An acetabular reamer is used to cut a cavity into the pelvic bone into which the socket portion of an artificial hip joint can be inserted. Patella reamers are used to shape the patella in knee operations. Glenoid reamers are used to prepare shoulder sockets for insertion of artificial shoulder joints. The dimensions and shape of the cavity cut are critical in many such operations, as the tolerances between the cavity and the socket portion of a joint must be small to ensure proper function. This is especially true with the newly available "cementless" prostheses. In "cementless" prostheses, the socket portion is frictionally fit into a cavity, placing added importance upon accurate cavity dimensions and tolerances.

Known methods of making reamers include forming holes in the reamers, from which a peripheral portion of the hole subsequently forms a cutting edge that is sharpened. Circular holes have been used, with the cutting edge being a curved portion of the periphery of the hole. Partly circular holes also have been used, in which the cutting edge is defined by a chord of the circle. "D" shaped holes are also known. Still other known shapes for the holes are based upon closed geometric shapes other than circles, such as ellipsoids. In these versions, the cutting edge is straight in the plane of the hole, with the cutting edge being both formed into the shape desired, and later sharpened. The cutting edges, however, in many situations cannot be shaped optimally, in that the opposite ends of the cutting edge are attached to the periphery of the hole. Thus, forming the cutting edge into any shape whatsoever naturally involves portions of the hole periphery, or portions of the cutting edge that are angular with other portions of the cutting edge both in planes generally parallel to and generally perpendicular to the reamer surface. It is therefore highly desirable to provide a new and improved reamer cutting edge, and method for making the same, by which the cutting edge may be shaped as desired. It is also highly desirable to provide a new and improved cutting edge for reamers by which more accurate cavity dimensions and smaller tolerances can be maintained, and a new improved method for making the same.

The cutting edges in reamers desirably have a long useful life. The shape of the cutting edge can influence both the useful life of the cutting and the ease by which it cuts. Thus, it is highly desirable to provide a new and improved reamer having cutting edges the shape of which is less limited by the structure of the reamer. It is also highly desirable to provide a new and improved reamer in which the cutting edge can be made to cut in shear. It is also highly desirable to provide a new and improved reamer with optimally shaped cutting edges.

In most operations in which surgical reamers are used, desirably, the bone chips cut by the reamer are saved, to be used during the operation to fill voids between the prosthesis and the hole formed by the reamer. It is known to save the bone chips within the reamer. Therefore, it is highly desirable to provide a new and improved reamer construction having means for saving the bone chips during an operation in which the reamer is used.

Reamers that are designed for repeated use require sterilization. Therefore, it is highly desirable to provide new and improved reamers which can be stripped in the field and sterilized for re-use, and which do not have crevices and other structure to hold bone chips and tissue from the operation which cannot be easily dislodged prior to sterilization.

Finally, it is highly desirable to provide a new and improved reamer construction and cutting edges therefore, and a method for making the same, which possess all of the above desired features.

SUMMARY OF THE INVENTION

It is an advantage of the invention to provide a new and improved reamer cutting edge, and a method for making the same, by which the cutting edge may be shaped as desired.

It is also an advantage of the invention to provide a new and improved cutting edge for reamers by which more accurate cavity dimensions and smaller tolerances can be maintained, and a new and improved method for making the same.

It is also an advantage of the invention to provide a new and improved reamer having cutting edges the shape of which is less limited by the structure of the reamer.

It is also an advantage of the invention to provide a new and improved reamer in which the cutting edge can be made to cut in shear.

It is also an advantage of the invention to provide a new and improved reamer with optimally shaped cutting edges.

It is also an advantage of the invention to provide a new and improved reamer construction having means for saving the bone chips during an operation in which the reamer is used.

It is also an advantage of the invention to provide a new and improved reamer that can be stripped in the filed and sterilized for re-use, and which does not have crevices and other structures to hold bone chips and tissue which cannot be easily dislodged prior to sterilization.

It is also an advantage of the invention to provide a new and improved reamer construction, cutting edges therefore, and a method for making the same which possess all of the above desired features.

In the broader aspect of the invention, there is provided a new and improved reamer having a plurality of openings therein. Each of the openings has a periphery and a cutting edge selected from the periphery. Opposite portions of the periphery are extended past the cutting edge, in a direction opposite to the direction of the opening, and transversely of the cutting edge, thereby forming spaced apart relief slots, whereby the cutting edge may be shaped as desired independently of the shape of the periphery.

BRIEF DESCRIPTION OF THE DRAWINGS

The above-mentioned and other features and advantages of this invention, and the manner of attaining them, will become more apparent, and the invention will be better understood, by reference to the following description of embodiments of the invention taken in conjunction with the accompanying drawings, wherein.

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION OF THE INVENTION

Figure 1:
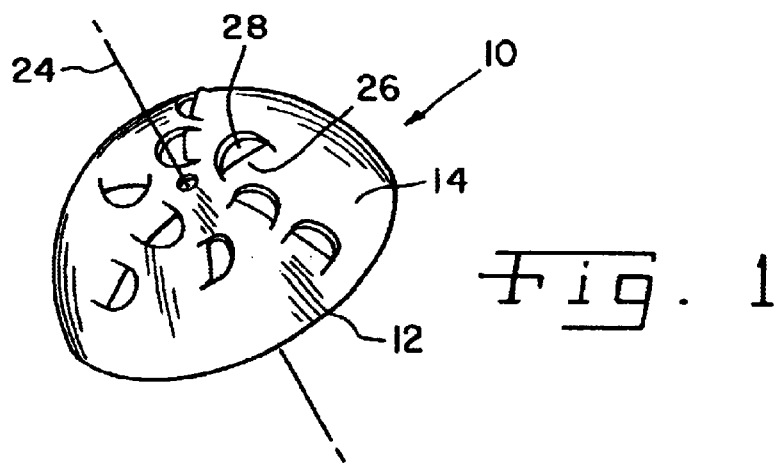
FIG. 1 is a perspective view of an acetabular reamer cup of the invention.
Figure 2:
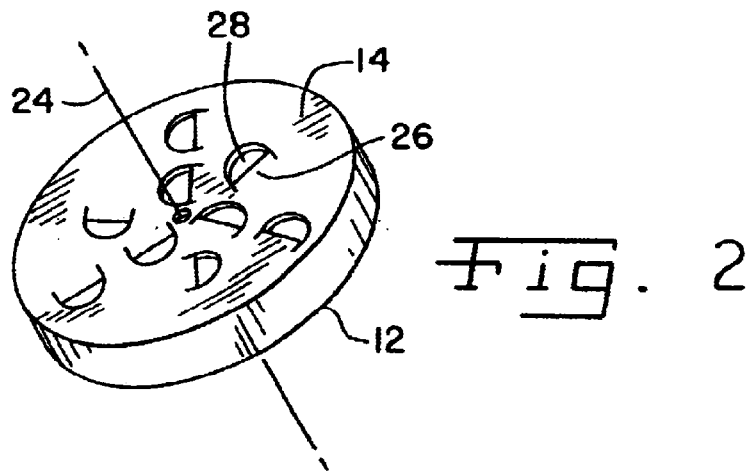
FIG. 2 is a perspective view of a patella reamer of the invention.
Figure 3:
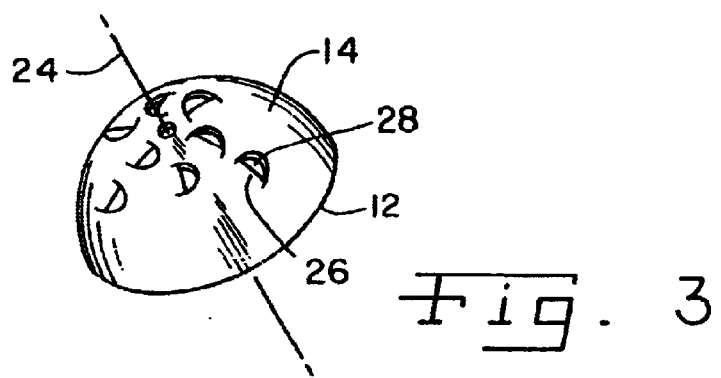
FIG. 3 is a perspective view of a glenoid reamer of the invention.
Figure 4:
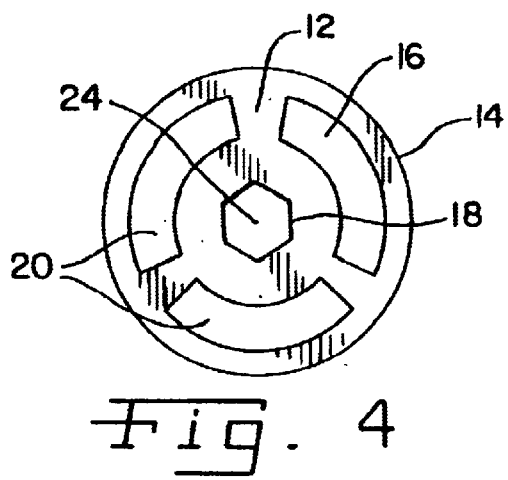
FIG. 4 is a bottom plan view of one of the reamers of the invention.

Reamers 10 of the present invention have a bottom 12 and a spaced reamer surface 14 that can be either part spherical, as surface 14 shown in FIG. 1 and 3, or essentially planar, as shown in FIG. 2. Bottom 12 may be flat or angled rearwardly so as to eliminate internal 90° angles that could retain contaminants. Reamer surface 14 and bottom 12 together define an interior debris compartment 16 (FIGS. 4–6) within each of reamers 10. Debris compartment 16 is utilized to collect bone chips and other debris during surgery. Bottom 12, in one version, has a tool driver opening 18, which is concentric with cutting surface 14. Surrounding tool driver opening 18 may be a plurality of voids 20 that are provided for clearance of debris during use.

Each reamer 10 has an axis of rotation, designated in the drawings by line 24, about which reamer 10 is rotated during use. Reamer 10 has a spirally arranged pattern of outwardly extending cutters 26 and adjoining openings 28. Each cutter 26 is preceded during rotation by an opening 28. Each opening 28 sweeps an area before a respective cutter 26. Each cutter 26 is formed from reamer 10 of a material capable of holding a sharpened edge through a reasonable period of time. Stainless steel is one of the suitable materials for reamers 10.

Figure 5:
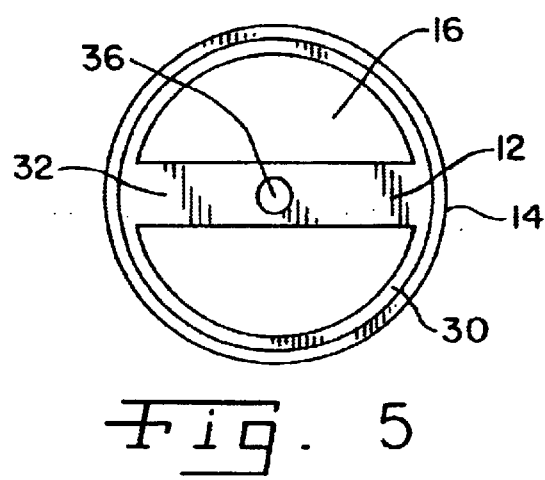
FIG. 5 is a modified bottom plan view of the reamers of the invention.
Figure 6:
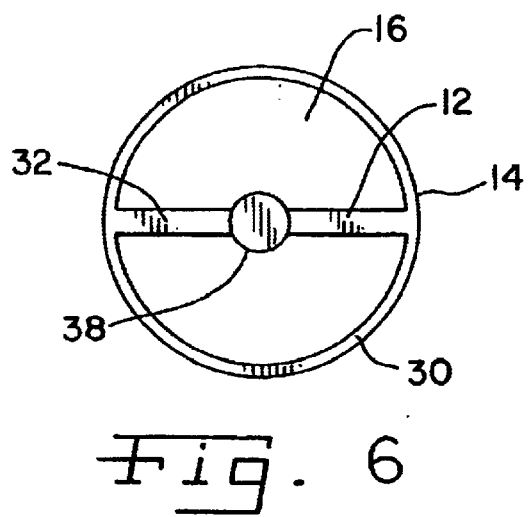
FIG. 6 is a second modified bottom plan view of the reamers of the invention.

Instead of a tool driver opening 18, bottom 12 may comprise a disk having a peripheral annular portion 30, a diametrally extending bar 32 and either a hole 36 centrally located in bar 32 as shown in FIG. 5, or a centrally located disk 38, as shown in FIG. 6. Annular portion 30 may be eliminated, provided the material of reamer 10 is sufficiently strong to resist misshaping during handling.

Figure 7:
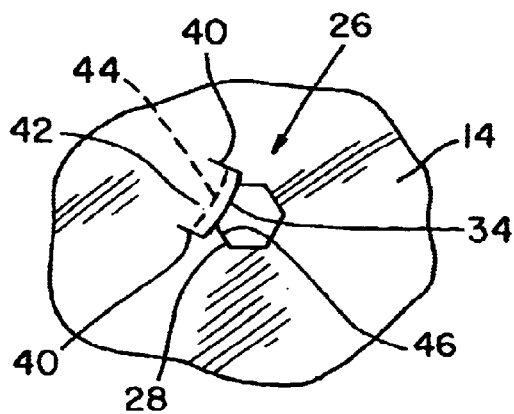
FIG. 7 is an enlarged top view of one of the cutters of the invention.
Figure 8:
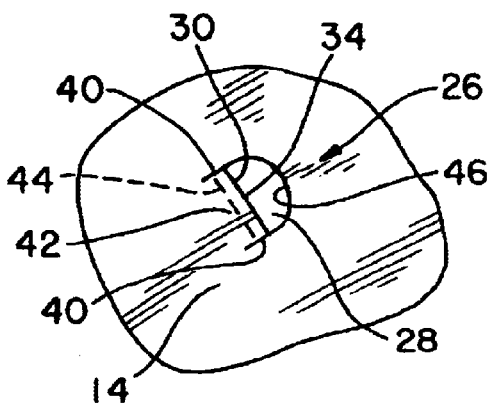
FIG. 8 is a modified cutter of the invention.
Figure 9:
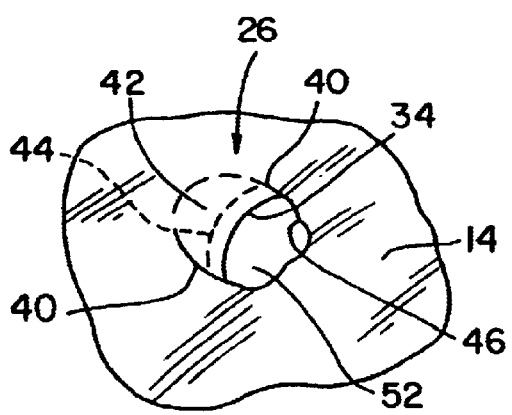
FIG. 9 is second modified cutter of the invention.

Each reamer 10 has a plurality of cutters 26 spirally arranged on reamer surface 14. Each cutter 26 has a continuous cutting edge 34. Edges 34 may be generally straight in planes perpendicular to the reamer surface 14 or tangential or parallel to the tangential plane with respect to the reamer surface 14. Cutting edges 34 may also be curved in planes perpendicular to the reamer surface 14 or parallel or tangential to the reamer surface 14. Further, the curvature may be convex as shown in FIG. 9, concave as shown in FIG. 7 or of other complex shapes not shown. As will become apparent from the description following, there need be no relationship between the shape of cutting edges 34 and the shape of reamer surface 14. In fact, one may be curved and the other straight, or both may be curved in the same or opposite directions, as will become evident hereinafter.

Once the size and shape of the opening 28 are determined, the length of cutting edge 34 is also determined. The length of cutting edge 34 may be diametral or chordal in relationship of openings 28 that are of circular geometry. In other closed geometrical shapes, edges 34 may be either chordal or may be diametral of inscribed circles or superscribed circles of the geometrical shape which are defined herein as "chordal openings." Openings 28 may be of a curved or irregular shape in both planes perpendicular to the reamer surface 14, as desired, each opening 28 having a periphery 46.

Subsequent to formation of opening 28, and the identification of the portion of opening 28 forming cutting edge 34, opposite portions of the periphery are extended past cutting edge 34 in a direction opposite the direction in which cutting edge 34 faces, and away from opening 28. This extension of the opening periphery past cutting edge 34 forms relief slots 40, which are spaced apart by cutting edge 34. Relief slots 40 may be parallel to each other, or angular to each other. Relief slots 40, together with cutting edge 34 define a cutter tongue 42. The longitudinal dimension of tongue 42, in the direction of relief slots 34, defines the magnitude of height and spacing that edge 34 may be positioned from the reamer surface 14. In a specific embodiment, relief slots 40 may be of the same lengths in embodiments in which the cutting edge 34 is symmetrical to the rotational direction, or relief slots 40 may be of different lengths for embodiments in which cutting edge 34 is asymmetrical in the direction of rotation. By removing material from the cutting edge in addition to the material removed from opening 28, the cutting edge may be shaped in many desired shapes.

In a specific embodiment, cutting edges 34 may have a curvature in planes perpendicular to reamer surface 14 and in planes tangential or parallel to a plane tangential to reamer surface 14. Doubly curved cutting edges 34 are always in shear cutting position, irrespective of the placement of cutting edge 34 with respect to surface 14 and the rotation of reamer 10.

The rise of cutting edges 34 above reamer surface 14 is limited only by the length of relief slots 40 on opposite sides of cutting edge 34, and the hardness of the bone being cut. Each tongue 42 can be similarly shaped and raised, so that cutting edges 34 are each a similar height above surface 14. Tolerances of elevation within plus or minus 0.006 inch can be achieved. Alternatively, tongues 42 can be elevated and shaped differently, to place various edges 34 at different heights above surface 14. Within the limits of relief slots 40, cutting edges 34 may be positioned respective to reamer surface 14 and shaped as desired without reference to reamer surface 14. Further, cutting edges 34 may be of any shape irrespective of the shape of openings 28 preceding cutting edge 34. Openings 28 may be punched, cut or otherwise formed prior to the sharpening of cutting edge 34, or may be cut during the formation of openings 28. Openings 28 may be of any closed geometrical shape, including part circular, triangular, rectangular or square, octagonal, hexagonal, heptagonal, nonagonal or decagonal, or may include both curved and straight boundary portions so as to define openings 28 of irregular shape.

By a cutting, punching or other machining operation subsequent to the formation of reamer 10 and the formation of openings 28, tongue 42 and cutting edge 34 may be shaped as desired. In specific embodiments, tongue 42 and cutting edge 34 may be concavely curved, convexly curved or irregularly shaped as desired. It is highly desirable in positioning cutting edge 34 above reamer surface 14 and shaping cutting edge 34 to place cutting edge 34 so as to cut the bone in shear rather than "head on", thereby improving the reaming accuracy that can be accomplished by the reamer operation. Head on positioning of cutting edges 34 decreases the useful life of cutting edge 34 and allows cutting edge 34 to chip the bone rather than to cut the bone.

Cutting edges 34 are positioned to follow the other cutting edges 34 upon rotation. Each of cutting edge 34 sweeps an area overlapped by one or more of the other cutting edges 34. In a specific embodiment, the following cutting edges 34 overlap the leading cutting edges 34 a total of about one and one-half times.

In the method of the invention, reamer 10 is formed of a material capable of holding a sharpened edge through a reasonable period of use. Stainless steel is one of the materials that are suitable for making reamer 10. Reamer 10 may be shaped by drawing or by any suitable forming or shaping method.

Either before or after reamer 10 is shaped, axis of rotation 24 is located, and the blank reamer 10 is perforated with a plurality of openings 28, each having a periphery 46. A portion of periphery 46 is designated as cutting edge 34. Openings 28 may be formed in reamer 10 by punching, drilling or the like. If openings 28 are formed by a method that produces burrs, openings 28 must be deburred. While it is convenient to make openings 28 round, the method of the present invention is not limited to round openings 28. Openings 28 may be of any closed geometric shape, i.e., circular, rectangular, square, triangular, hexagonal, octagonal, or nonagonal or decagonal or any irregular closed shape. Openings 28 are cut in a pattern that defines a spiral or a spoked wheel shape upon rotation of reamer 10. See FIG. 1.

After cutting edge 34 has been designated, periphery 46 of opening 28, on the opposite ends of cutting edge 34, is extended in the direction away from the direction cutting edge 34 faces, away from opening 28, thereby forming relief slots 40 and defining tongue 42. Relief slots 40 may be formed by the same or different methods as the openings 28 are formed. In a specific embodiment, openings 28 and relief slots 40 are formed by laser cutting. Relief slots 40 have a minimal width. In general, the width is less than that which would allow bone chips or debris to catch on, become lodged in or to pass through the slots 40. Widths of between about 0.0005 inch to about 0.040 inch are acceptable in the preferred embodiment.

As cutting edges 34 are formed of a part of the periphery of opening 28, cutting edge 34 will have the initial shape of opening 28. After relief slots 40 are cut, cutting edge 34 is independent of opening 30 and can be raised and shaped as desired. Further, the entirety of tongue 42 may be raised and shaped as desired. In specific embodiments, cutting edges 34 may be straight, curved so as to be convex, curved so as to be concave, or shaped to have a complex curve such as a sign wave curve or other complex curves. Further, either straight cutting edges 34 or curved cutting edges 34 may be aligned so as to be angular with respect to relief slots 40, or generally perpendicular to relief slots 40 as desired. The shaping of cutting edges 34 may be done at the time openings 28 are formed, or at a later time.

Tongues 42 are deformed outwardly to position cutting edges 34 above reamer surface 14 before, after or simultaneously with the shaping of cutting edges 34 and tongues 42. In specific embodiments, tongue 42 is curved or otherwise formed to provide tongue 42 with additional strength. In specific embodiments, tongues 42 are shaped to define planes perpendicular to the reamer surface 14. The shapes may have straight lines, such as a plurality of interconnected peaks and valleys, or curved lines such as a concave curve, or a convex curve or a complex curve such as a sign wave or other irregular curves.

In a specific embodiment, cutting edges 34 and tongues 42 are deformed outwardly each individually, and this is repeated for each and every opening 28.

In a specific embodiment of the invention as described herein, cutting edges 34 extend over a substantial portion of periphery 46 of openings 28, but substantially less than the entire periphery 46. In specific embodiments of the invention, cutting edges 34 extend between about 270° and about 30° of periphery 46. In a specific embodiment of the invention, cutting edges 34 extend about 30° of periphery 46.

Figure 10:
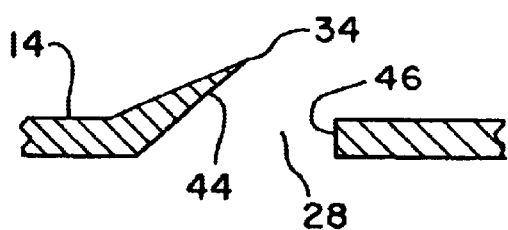
FIG. 10 is an enlarged side view of one of the cutting edges.

Before or after the cutting edges 34 are properly positioned, each cutting edge 34 can be sharpened by inserting a rotary "rats tail" grinder within each of openings 28 to form a bevel 44 to the requisite sharpness for cutting bone. Each bevel 44 faces inwardly of reamer 10, as shown in FIG. 10. Alternatively, smoothing and raising steps disclosed in U.S. Pat. No. 4,811,632 can be used. By this technique, all cutting edges 34 are similarly raised when tongues 42 are deformed outwardly.

In a specific embodiment, the shaping of tongue 42 and cutting edge 34, and the raising of tongue 42 are accomplished by punching operations which can be accurately controlled to control the tolerances of cutting edges 34. In specific embodiments, tongues 42 are raised to an angle from between about 15 degrees to about 80 degrees, relative to surface 14.

Relief slots 40 permit raising and shaping of tongues 42 without deforming the surrounding material, and the dimensional tolerances are set by the raising of tongues 42. Thus, the tolerances are significantly smaller than those available using other manufacturing techniques. In the method of the invention, each cutting edge 34 may be shaped as desired. Cutting edges 34 may be totally independent of the shape of reamer surface 14, as there is no portion of tongues 42 adjacent cutting edges 34 that are connected to reamer 10. Thus, cutting edges 34 may be shaped in any way. Cutting edges 34 may be formed into shapes which the cutting edges disclosed in U.S. Pat. No. 4,811,632 or U.S. Pat. No. 5,709,688 cannot be formed. Cutting edges in each of U.S. Pat. Nos. 4,811,632 and 5,709,688 are limited by the cutting edges being attached to the reamer body at the opposite ends of the cutting edges. Cutting edges 34 of this invention are not attached to the reamer body at the opposite ends of the cutting edges 34, and thus may be elevated above reamer surface 14, and may have a shape totally distinct from the shape of surface 14. In a specific embodiment, for example, this allows an acetabular reamer cup having a generally spherical surface 14 to have cutting edges 34 that are straight. Similarly, in other specific embodiments, reamer surface 14 may be planar, as in a patella reamer, and cutting edges 34 may be curved in one or more of the planes parallel to the surface 14 or perpendicular thereto, so as to place cutting edges 34 always in shear during use.

The support for cutting edges 34 also can be varied by varying the length of relief slots 40, and by varying the shape of tongue 42, and the material from which reamer 10 is made. In general, there are no limitations as to the shape of cutting edges 34, the positioning of cutting edges 34 with respect to surface 14, or the height at which cutting edges 34 may be positioned from surface 14, other than as limited by the size of tongues 42 and the material from which reamer 10 is made.

Comparing reamer 10 of the invention with prior reamers, bone may be cut with smaller tolerances than heretofore possible because of the greater consistency among cutting edges 34, and the accurate positioning and shaping of cutting edges 34. With reamer 10 of the invention, tolerances of plus or minus 0.003 inch can be achieved, whereas in other reamer cups tolerances of plus or minus 0.010 inch were common. Improved accuracy is desired with the new "cementless" hip joints. Additionally, the improved sharpness of cutting edges 34 can be achieved, for more accurate reaming, and more efficient bone removal, as evidenced by the following tests performed with the invention.

Testing Equipment

Pattern mahogany in squares of approximately 2.75 inches, with a 0.500 inch pilot hole.

Enco milling and drilling machine Model No 91034, available from Enco Manufacturing Co. Chicago, Ill., belted to operate at 300 rpm, and having a material work piece vise, an actuatable shaft moveable toward and away from material held in the vice, and equipped with a dial indicator of travel distance from 0.001 inch to 1.00 inch.

A timer such as a West Bend electronic timer, Cat. No. 4000, available from The West Bend Company, West Bend, Wis. 53095.

Testing Procedure

A shaft assembly 14 was selected to best fit the cup to be tested, and secured to the cup.

A proper mahogany test block was selected. When testing a reamer of 40–45 mm cut, a new block was used. When testing a 46 mm or larger cup, a previously used block may have been reused. For example, if a mahogany block had been used to test a 54 mm cup, it was used to test a 56 mm cut. The entire spherical cutting path was tested.

The mahogany block was secured in the vise. The shaft with cup attached was lowered down on top of the block, and centered on the pilot hole.

The timer was set for a period of 5 seconds for any cup 50 mm or smaller; 7 seconds for 51 mm to 59 mm, and 10 seconds for grater cups 60 mm and up. Reaming was begun, with the reamer operated against the mahogany block for the established trial duration.

A minimum cut of 0.350 inch was deemed be acceptable. Depths were measured from the dial indicator.

The following reaming results were obtained:

| Rim Size | Time of Cut | Prior Art | Cutting Edges 34 |
| --- | --- | --- | --- |
| 42 | 7 Seconds | .460" | .920" |
| 44 | 7 Seconds | .405" | .810" |
|  | 5 Seconds | .359" | .718" |
| 48 | 5 Seconds | .150" | .299" |
| 56 | 7 Seconds | .045" | .091' |
| 58/57 | 7 Seconds | .145" | .292" |

Reamer 10 produced by the method of the invention is used by connecting it to the shaft of a tool driver such as disclosed in U.S. Pat. Nos. 4,811,632 and 5,709,688. Bottom 12 of each reamer 10 of the invention has a structure such as those shown in FIGS. 4, 5 and 6 that allow reamers 10 to be connected to the appropriate tool driver. While rotating, reamer 10 is pressed against the bone of a patient, to cut the bone as desired.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A reamer having a plurality of openings therein, each of said openings having a periphery and a cutting edge selected from said periphery, each of said cutting edges being bounded by opposite portions of said periphery, said opposite portions including relief slots extending past said cutting edges in a direction oppositely of the direction that the cutting edges face, whereby said cutting edges are isolated from said periphery and may be shaped as desired independently of the shape of said periphery, and wherein each of said cutting edges has an exterior surface and a beveled tapered portion intersecting said exterior surface at said cutting edge, said tapered portion facing interior of said reamer.

2. The reamer of claim 1 wherein said openings correspond to said cutting edges, respectively.

3. The reamer of claim 1 wherein said openings are of the group of partial geometric closed shapes consisting of circles, hexagons, squares, rectangles, pentagons, triangles, heptagons, octagons, nonagons and decagons, and both regular and irregular closed geometric shapes.

4. The reamer of claim 1 wherein said cutting edges are straight.

5. The reamer of claim 1 wherein said cutting edges are curved in the surface of said openings.

6. The reamer of claim 1 wherein said cutting edges are curved in planes perpendicular to the surface of said opening.

7. The reamer of claim 1 wherein the surface of said opening defines a spherical surface.

8. The reamer of claim 1 wherein the surface of said opening defines a planar surface.

9. The reamer of claim 1 wherein the surface of said openings defines a surface of the group of surfaces consisting of a spherical surfaces, planar surfaces, irregular surfaces and conical surfaces.

10. The reamer of claim 1, wherein said relief slots have a length sufficiently long to define a cutter tongue therebetween, and to allow said cutter tongue to be bent upwardly relative to said surface.

11. The reamer of claim 10 wherein said relief slots have a width sufficiently narrow to preclude cutting debris from being positioned therein.

12. The reamer of claim 1 wherein each of said cutting edges and said relief slots associated therewith define a cutter tongue.

13. The reamer of claim 12 wherein an angle formed between said cutter tongue and said surface is between about 15 degrees and about 80 degrees.

14. The reamer of claim 1 wherein said cutting edges are formed by cutting chordal openings in the surface of a reamer, cutting two equal distant relief slots generally transverse to the flat side of said chordal openings at the opposite ends of the chord thereby forming a tongue, bending said tongue upwardly in relation to said surface of said opening whereby debris cut by said cutting edge passes through said opening preferentially to said relief slots.

15. The reamer of claim 1 wherein said reamer is an acetabular reamer cup.

16. The reamer of claim 1 wherein said reamer is a patella reamer disc.

17. The reamer of claim 1 wherein said reamer is a glenoid reamer cup.

18. A method for making reamers comprising the steps of fabricating a reamer blank, perforating a plurality of openings through said reamer blank, each of said openings being surrounded by a periphery, designating a portion of said peripheries as cutting edges, extending said peripheries on opposite ends of said cutting edges away from said openings, thereby forming relief slots; defining tongues having a distal end corresponding to said cutting edges, forming said tongues to accurately position said cutting edges from said reamer blank surface and sharpening said cutting edge as desired.

19. The method of claim 18 further comprising shaping said cutting edges as desired.

20. The method of claim 18 further comprising shaping said tongues as desired.

21. The method of claim 18 wherein said perforating step is performed before said fabricating step.

22. The method of claim 18 wherein said fabricating step is performed before said perforating step.

23. The method of claim 18 wherein said perforating step and said extending step are performed before said fabricating step.

24. The method of claim 18 wherein said fabricating step is performed before said perforating step and said extending step.

25. The method of claim 18 wherein said step of perforating openings comprises creating shapes from the group of closed geometric shapes consisting of circles, hexagons, squares, rectangles, pentagons, triangles, heptagons, octagons, nonagons and decagons.

26. The method of claim 18 further comprising the step of deburring said openings.

27. The method of claim 18 including shaping said cutting edges all similarly.

28. The method of claim 18 including shaping said tongues all similarly.

29. The method of claim 18 wherein said forming tongues includes raising the height of each said cutting edge from said surface similarly, and within plus or minus 0.006 inches.

30. The method of claim 18 including extending cutting edges between 30° and 270° around the respective one of said openings.

31. The method of claim 18 wherein said designating the cutting edges includes orienting the edges spirally on said surface of said reamer.

32. The method of claim 18 including shaping said cutting edges generally straight and shaping said tongues in a curve.

33. The method of claim 18 including shaping said tongues concavely curved.

34. The method of claim 18 including shaping said tongues convexly curved.

35. The method of claim 18 wherein said forming relief slots includes creating slots sufficiently narrow to inhibit bone chips and debris to pass therethrough.

36. The method of claim 18, wherein said forming relief slots includes creating cuts from about 0.0005 inch to about 0.040 inch in width.

37. The method of claim 18 including shaping said cutting edges and shaping said tongues independent of the shape of said opening and the shape of said surface.

38. The method of claim 18 including shaping said cutting edges and shaping said tongues before said forming step.

39. The method of claim 18 including shaping said cutting edges and shaping said tongues are shaped after said forming step.

40. The method of claim 18 wherein said cutting edges are supported by said tongue and further comprising the step of altering said support by shaping said tongue.

41. The method of claim 18 including positioning all said cutting edges at the same elevation from said reamer blank surface, plus or minus about 0.003 inches.

* * * * *